(12) United States Patent
Foster et al.

(10) Patent No.: US 9,360,164 B2
(45) Date of Patent: Jun. 7, 2016

(54) PARTICLE MANIPULATION SYSTEM WITH STAY-WET ALGORITHM

(71) Applicant: Owl biomedical, Inc., Goleta, CA (US)

(72) Inventors: John S Foster, Santa Barbara, CA (US); Nicholas C. Martinez, Santa Barbara, CA (US); Kevin E. Shields, Santa Barbara, CA (US); Jaquelin K. Spong, Mount Jackson, VA (US)

(73) Assignee: Owl biomedical, Inc., Goleta, CA (US)

( * ) Notice: Subject to any disclaimer, the term of this patent is extended or adjusted under 35 U.S.C. 154(b) by 170 days.

(21) Appl. No.: 14/167,566

(22) Filed: Jan. 29, 2014

(65) Prior Publication Data

US 2015/0211685 A1    Jul. 30, 2015

(51) Int. Cl.
*F17D 3/01*    (2006.01)
*B01L 3/00*    (2006.01)
*G01N 35/08*   (2006.01)

(52) U.S. Cl.
CPC ............. *F17D 3/01* (2013.01); *B01L 3/502723* (2013.01); *B01L 3/502738* (2013.01); *B01L 3/502761* (2013.01); *B01L 3/502715* (2013.01); *B01L 2200/0647* (2013.01); *B01L 2200/0652* (2013.01); *B01L 2200/143* (2013.01); *B01L 2200/146* (2013.01); *B01L 2300/0627* (2013.01); *B01L 2300/0663* (2013.01); *B01L 2400/0622* (2013.01); *B01L 2400/0644* (2013.01); *G01N 35/085* (2013.01); *Y10T 137/0318* (2015.04); *Y10T 137/8342* (2015.04)

(58) Field of Classification Search
CPC .................... B01L 3/502723; B01L 3/502761; F17D 3/01; G01N 35/085
USPC .......................................................... 422/73
See application file for complete search history.

(56) References Cited

U.S. PATENT DOCUMENTS

| | | | |
|---|---|---|---|
| 5,633,168 A | 5/1997 | Glasscock et al. | |
| 8,266,950 B2* | 9/2012 | Kaduchak | G01N 15/1404 73/570.5 |
| 2009/0050569 A1* | 2/2009 | Jung | B01L 3/502776 210/695 |
| 2012/0190104 A1* | 7/2012 | Foster | B01L 3/502738 435/288.7 |
| 2012/0255373 A1 | 10/2012 | Foster et al. | |
| 2014/0097129 A1* | 4/2014 | Foster | B01L 3/502761 209/579 |
| 2014/0299221 A1* | 10/2014 | Lopez | A61M 5/14228 141/1 |

\* cited by examiner

*Primary Examiner* — Jill Warden
*Assistant Examiner* — Jacqueline Brazin
(74) *Attorney, Agent, or Firm* — Jaquelin K. Spong

(57) ABSTRACT

A MEMS-based particle manipulation system which uses a particle manipulation stage and a sensor to detect when the sample volume is exhausted or nearly exhausted. The sensor sends a signal to a fluid control means that reverses the pressure between one of the output channels and the input channels, to keep the surfaces wet with a volume of the sample fluid. This volume can be maintained in the channel until an operator intervenes, or it can be repeatedly shuttled back and forth between the input channel and an output channel. By keeping the channels wet, material from the sample stream does not become adhered to the channel walls, which might otherwise irreversibly change or damage the device.

19 Claims, 8 Drawing Sheets

PARTICLE MANIPULATION SYSTEM WITH STAY-WET ALGORITHM

CROSS REFERENCE TO RELATED APPLICATIONS

This U.S. patent application is related to U.S. patent application Ser. No. 14/104,084, filed Dec. 12, 2013, and incorporated by reference.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for moveable MEMS devices may be thermal, piezoelectric, electrostatic, or magnetic, for example. MEMS devices may also be made which manipulate particles in a fluid stream passing by or through the MEMS device.

Such a particle manipulation device may be a MEMS moveable valve, which can be used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems have been proposed as an improvement to existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from the nozzle, the droplets are separated into different bins electrostatically, based on the fluorescence signal from the tag. Among the issues with these systems are cell damage or loss of functionality due to the decompression, difficult and costly sterilization procedures between samples, inability to sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A MEMS-based cell sorter may have substantial advantages at least in terms of size, cost and complexity over existing FACS flow cytometers. A number of patents have been granted which are directed to such MEMS-based cell sorting devices. For example, U.S. Pat. No. 6,838,056 (the '056 patent) is directed to a MEMS-based cell sorting device, U.S. Pat. No. 7,264,972 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Each of these patents is hereby incorporated by reference.

Such particle sorting devices may be examples of a broader category of particle manipulation systems, which may perform some manipulation on the particles passing by in a fluid stream. The stream may include target particles as well as non-target materials. The manipulation may be to apply a charge, apply a force, apply a field, or apply laser light, to the target particles, for example. The purpose may by to identify, alter or destroy the target particles. Alternatively, the purpose may be to distinguish target particles from non-target materials, and/or to separate them from the remainder of the fluid stream.

SUMMARY

Many if not all such microfabricated manipulation devices use small, microfluidic channels to transport a sample fluid from an upstream input channel, past the particle manipulation device, to a downstream output channel. When using a microfluidic device, and the fluids include particles of any kind, then a wetting inside the microfluidic channels followed by a drying may result in a very strong adhesion of the particles to the microfluidic channel walls. This is especially true of biological material, such as blood or cellular suspensions. The adhesion of material may cause an undesired, and possibly irreversible, change to the device. The unwanted changes include an increase in subsequent fluidic resistance, contamination of any subsequent sample introduced into the device, and a change in the flow patterns within the device. As disclosed here, this outcome may be avoided by the use of a sensor that detects the "run-dry" condition and invokes a "stay-wet" algorithm in response. The stay-wet algorithm may include measures that ensure the device maintains a wet condition, or otherwise avoids damage due to the stoppage of flow.

Accordingly, the particle manipulation system may include a particle manipulating device, at least one microfabricated input channel upstream of the particle manipulating device and at least one microfabricated output channel downstream of the particle manipulating device, through which a sample fluid flows, a sensor that detects a dry condition within at least one of the microfabricated channels and puts out a signal when the condition is detected, and a fluid control means for establishing a controlled forward flow between the at least one microfabricated input channel and at least one microfabricated output channel, and then reversing the flow between the output channel and the input channel upon receiving the signal from the sensor.

In one embodiment, the particle manipulation system using the stay-wet system may include microfluidic channels and a microfabricated (MEMS) cell sorting device, wherein a small, microfabricated valve separates one or more target particles from other components of a sample stream. The cell sorting device may redirect the particle flow from one channel into another channel, when a signal indicates that a target particle is present. This signal may be photons from a fluorescent tag which is affixed to the target particles and excited by laser illumination in an interrogation region upstream of the cell sorting device. Thus, the cell sorting device may be a particle or cell sorter operating on a fluid sample confined to a microfabricated fluidic channel, but using detection means similar to a FACS flow cytometer. Such a system may be equipped with a run-dry sensor and a controller which invokes the stay-wet algorithm upon receiving the signal from the run-dry detector, indicating that the microchannels are, or imminently will be, running dry.

In another embodiment, the microfabricated particle manipulation system may be a sorting device using a microfabricated valve having one input sample stream and at least two output channels, a sort channel for the target particle and a waste channel for the non-target particles. The microfabricated valve may be formed on the surface of a substrate, and may move in a plane substantially parallel to that surface. At least one of the microfabricated fluidic channels, however, may be oriented out of this plane, such that the fluid within this channel does not flow in the same plane as the fluid in the input channel. This valve may sort a target cell (cancer cell, sperm cell, stem cell for example) from the other components of a fluid stream. The microfabricated valve may be actuated magnetically or electromagnetically, to redirect the flow in response to the detection of a target particle in the channel. The valve directs the flow into a sort channel rather than a waste channel. The stay-wet particle sorting system may make use of this out-of-plane valve in particular, because the architecture of the out-of-plane valve has especially low resistance to the reverse (backward) flow of fluid through the microfabricated device. As before, the system using this microfabricated valve may also be equipped with a run-dry sensor and a controller which invokes the stay-wet algorithm upon receiving the signal from the run-dry detector, indicating that the microchannels are, or imminently will be, running dry.

Many different sorts of sensing mechanisms may be used to sense the run-dry condition based on any number of effects. Such effects include capacitance, voltage, pressure, mechanical forces, acoustics, fluid pump characteristics, optical characteristics, which may change when the device goes from a wet state to a dry state, to name just a few. Alternatively, in a data logging system such as a cell sorter, the data itself may indicate when the system is about to run-dry, and the system may then invoke the stay-wet algorithm. In another alternative, the condition of a fluid reservoir may be monitored to anticipate exhaustion of the fluid supply. The stay-wet algorithm may include the reversal of flow within the device until all passages are wet. In addition, the stay-wet algorithm may include reducing, altering or disabling an output of an interrogation laser; reducing, altering or disabling a power supply output; reducing, disabling or reversing a pump output; sounding an audible alarm; and sending a warning message to a computer monitor.

These and other features and advantages are described in, or are apparent from, the following detailed description.

BRIEF DESCRIPTION OF THE DRAWINGS

Various exemplary details are described with reference to the following figures, wherein.

DETAILED DESCRIPTION

The system described herein is a particle manipulation system which may make use of microchannel architectures, such as those disclosed in the aforementioned patents. More generally, the systems and methods describe a particle manipulation system with a stay-wet algorithm which is invoked when a sensor or detector detects a dry or imminently dry condition inside the microchannels. The detection of the dry or imminently dry condition may be based on fluid pressure, optical properties, viscosity, capacitance, acoustics and fluid resistance within at least one of the microfabricated channels. Alternatively, run-dry sensor may be a part of the data logging system such that the data itself may indicate when the system is about to run-dry, and the system may then invoke the stay-wet algorithm. In another alternative, the condition of a fluid reservoir may be monitored to anticipate exhaustion of the fluid supply. The stay-wet algorithm may include one or more steps intended to avoid or mitigate the dry or imminently dry condition, such as reversing the fluid flow and disabling lasers and power supplies.

In the figures discussed below, similar reference numbers are intended to refer to similar structures, and the structures are illustrated at various levels of detail to give a clear view of the important features of this novel device.

Figure 1A:
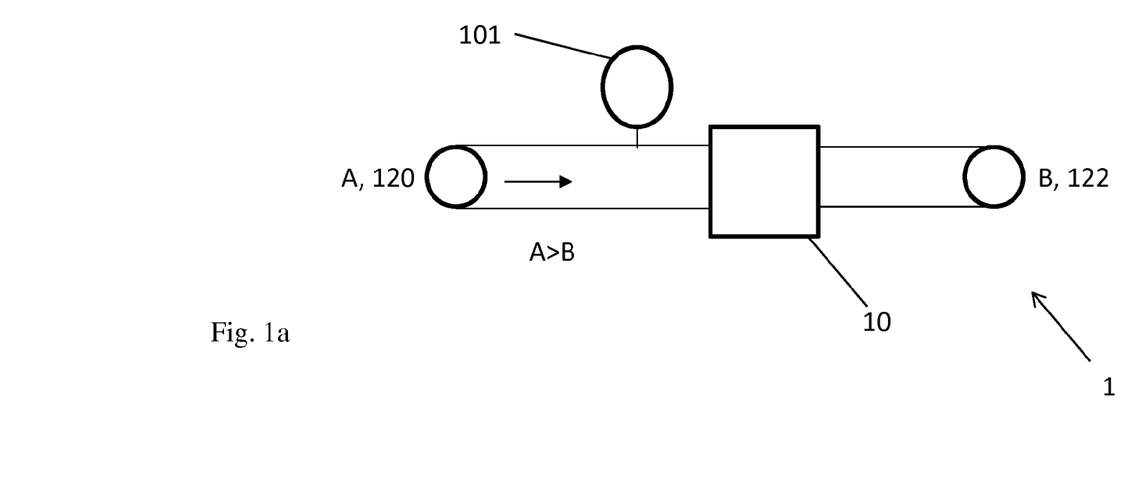
FIG. 1a is a simplified illustration of a stay-wet microfabricated particle manipulation system with a run-dry detector in forward flow.

FIG. 1a is a schematic illustration of a MEMS-based particle manipulation system 1 using microfluidic channels wherein the microfluidic channels stay constantly wet. The system may include a first channel 120, a detector 101, a particle manipulation stage 10, and an output channel 122. The particle manipulation stage 10 may be a device which alters, destroys or detects the particles in the sample stream 120. Downstream of the particle manipulation stage 10 and first channel 120 is one or more output channels 122. Each of the first channel 120 and the second channel 122 is associated with a first source of pressure A and a second source of pressure B. It should be understood that there may be an input fluid reservoir associated with the input channel 120 and an output fluid reservoir associated with output channel 122. Reference numbers 120 may refer to either the input reservoir and/or associated input channel and reference number 122 to the output reservoir and/or the associated output channel.

In one embodiment, the first microfluidic channel 120 may be an inlet channel 120 which directs a sample stream from the input reservoir, to the particle manipulation stage 10. The fluid stream in microfluidic channel 120 also flows through a run-dry detector 101. In this region, the sensor or detector 101 detects a dry or imminently dry condition occurring in the input channel. The detector may detect this condition based on changes in any number of properties, including optical, electrical, pressure, viscosity, capacitance, acoustics, fluid resistance, or other characteristics of the channel in the region of detector 101. The output channel 122 may direct the flow from the particle manipulation stage 10 to an output reservoir 122.

In one embodiment, detector 101 is an optical sensor or camera that detects a change in reflectance that occurs when the boundary goes to glass/air rather than glass/liquid, or silicon/air rather than silicon/liquid, depending on the material of the substrate upon the particle manipulation stage 10 is formed. In another embodiment, the detector 101 monitors pump characteristics and detects a change in power consumption, volumetric output, duty cycle or other characteristic of the pump which may result from a change in fluid volume within the microchannels as a result of air or ambient gas entering the microchannels. Therefore, although the sensor 101 is shown in FIG. 1a in association with the microfluidic passage 120, it should be understood that the sensor may alternatively be coupled to another microfluidic channel, or to the fluid control means or to the controlling computer, rather than to the microchannel 120, and that this depiction is exemplary only.

In one exemplary embodiment, the particle manipulation stage 10 may apply a charge to the target particle. In another exemplary embodiment discussed further below, the manipulation stage 10 may be an actuator, which diverts the target particle into a different flow path as the non-target particles.

Figure 1B:
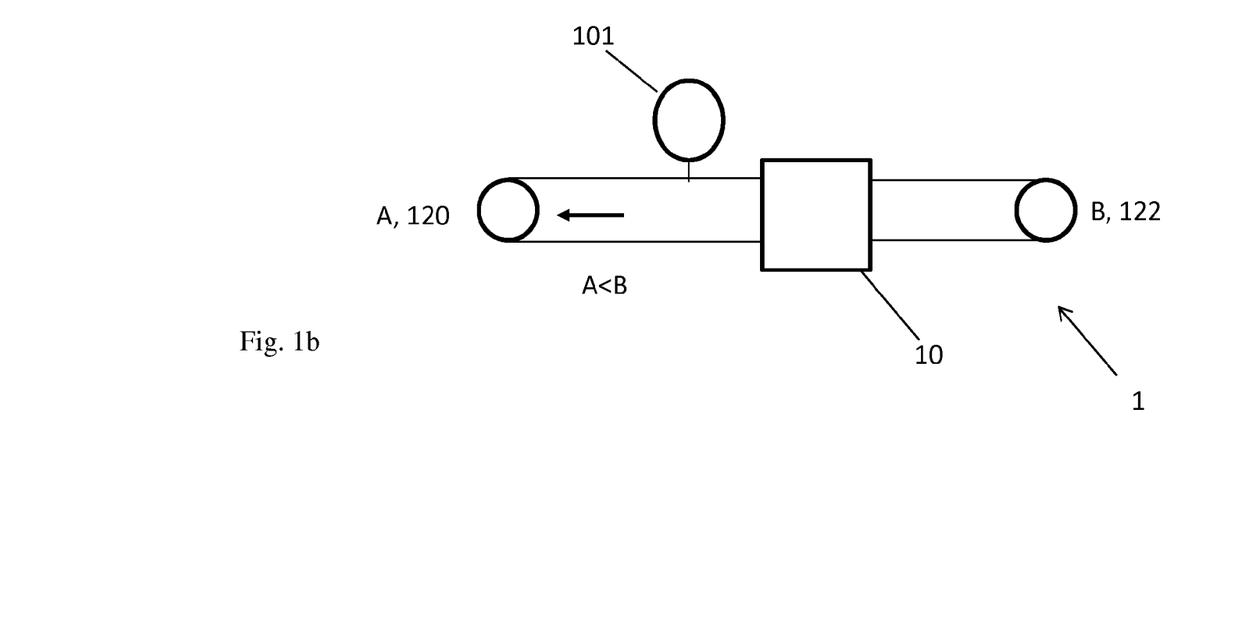
FIG. 1b is a simplified illustration of a stay-wet microfabricated particle manipulation system with a run-dry detector in reverse flow.

FIG. 1b is a schematic illustration of a MEMS-based particle manipulation system 1 using lithographically formed microfluidic channels wherein the microfluidic channels stay constantly wet. In FIG. 1b, the stay-wet algorithm has been invoked. As in FIG. 1a, the system may include a first channel 120, a run-dry detector 101, particle manipulation stage 10, and output channel 122, and each of the first channel 120 and the second channel 122 is associated with a first source of pressure A and a second source of pressure B. In FIG. 1b, the second pressure source B is greater than the first pressure source A, such that fluid flows backward through the system. The pressure has been reversed as a result of the run-dry detector 101 detecting a dry or imminently dry condition within the particle manipulation system and outputting a signal that invokes the stay-wet algorithm. The reversal of pressure and flow causes fluid from the output reservoir 122 to flow backward toward the input reservoir 120. The reversal of flow may serve to re-wet the channel walls to prevent irreversible changes as described above. The stay-wet algorithm may call for a volume of fluid to simply be stored in the manipulation system, until an operator can correct the situation by, for example, replenishing the sample fluid, or adding buffer fluid to the sample reservoir. The backward flow may also be accompanied by other measures which reduce or minimize the deleterious effects of the run-dry condition, depending on the application and the nature of particle manipulation stage 10. Such additional steps may include reducing, altering or disabling an output of an interrogation laser, disabling, reducing, reversing a pump output, sounding an audible alarm, and sending a warning message to a computer monitor. The exact details of the stay-wet algorithm may be tailored to suit the needs of the particle manipulation device and its distinguishing features, or the particular application.

For example, particle manipulation stage 10 may apply a charge to a passing particle. The stay-wet algorithm may include the cessation of charging or voltage supplied to the stage 10 in addition to reversing the flow of fluid.

Alternatively, particle manipulation stage 10 may apply a lethal dosage of radiation to destroy the viability of a selected passing particle. The stay-wet algorithm may include the cessation of this radiation, which might otherwise heat, boil or evaporate the fluid, and leave the constituent particles adhering to the channel walls.

Figure 2A:
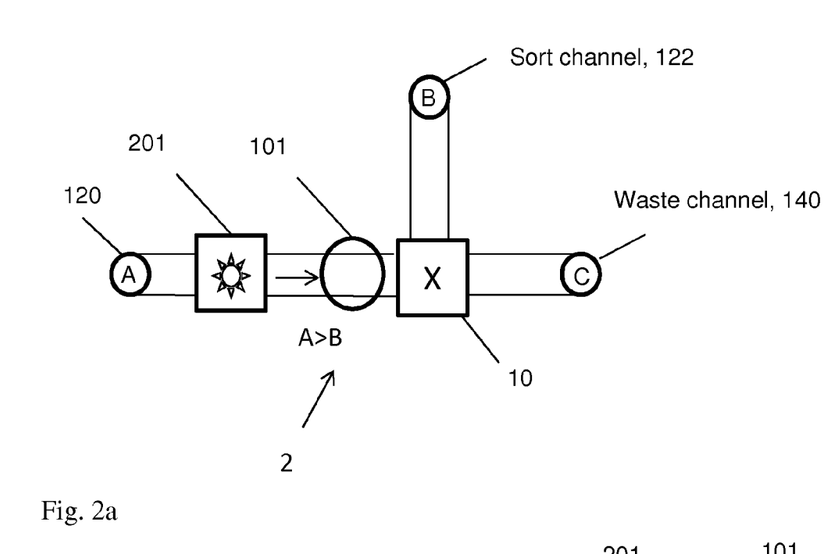
FIG. 2a is a simplified illustration of a stay-wet microfabricated particle sorting system with a run-dry detector in forward flow.

FIG. 2a is a schematic illustration of another particle manipulation system 2 using lithographically formed microfluidic channels that stay constantly wet. As before, an input channel 120 delivers fluid from an input reservoir to the particle manipulation stage 10. However, in FIG. 2a, two or more channels are formed at the output of the manipulation stage 10, forming an intersection point. One channel 122 may move in one path, a sort path, away from the manipulation stage 10, whereas another channel 140 may move in another path, a waste path, away from manipulation stage 10. Particle manipulation stage 10 may be a microfabricated particle sorter which direct a target particle into a sort channel 122 and allows nontarget material to flow into a waste channel 140. The movable member or particle manipulating device 110 moves from a first position to a second position in response to a force applied to the movable member, wherein the motion is substantially in a plane parallel to the surface, a sample inlet channel 120 formed in the substrate and through which a fluid flows, the fluid including one or more target particles and non-target material, wherein the flow in the sample inlet channel is substantially parallel to the surface. A plurality of output channels 122, 140 may be disposed in the substrate, into which the microfabricated member 110 diverts the fluid. In one embodiment, the flow in at least one output channel 140 is not parallel to the plane but is substantially orthogonal to it, and at least one output channel 140 is located directly below at least a portion of the movable member 110 over at least a portion of its motion.

The system may also include an interrogation region 201, in which a target particle is distinguished from non-target material. The distinguishing means may be based on any number of characteristics or attributes that distinguish the target particle from other material in the fluid stream. Although a laser interrogation is described below, it should be understood that other features may be used to distinguish the target particles. For example, the particles may be distinguished by differences in an electrical attribute, a hydrodynamic attribute, a magnetic attribute, an optical attribute, a thermal attribute, mass, or a mechanical attribute of the particle, to name just a few. This list is not meant to be exhaustive, but instead to provide examples of distinguishing systems which may be used with the manipulation stage 10 described herein.

In one embodiment, the distinguishing means 201 may be based on laser fluorescence. In this technique, the target particle may be a particular cell such as a stem cell, a cancer or tumor cell, a sex gamete, etc., which may be tagged with a fluorescent tag. Such tags are well known in the field and include for example fluorescein, Texas Red, phycobiliproteins, cyanine derivatives and rhodamine. While much of this disclosure is directed to this application, it should be understood that the systems and methods described herein are also applicable to other distinguishing mechanisms used to distinguish particles one from another. These mechanisms may be well known, or may yet be invented.

If a particle is tagged with a fluorescent tag, it may emit a photon in response to laser excitation, and this fluorescent radiation is an indication that a target particle is present in the laser interrogation region. If no fluorescent radiation is detected, the particle is likely an untagged, non-target particle. The particle manipulation stage 10 may sort, or divert, the tagged, target particle into the sort channel 122 and allow the non-tagged, non-target material to flow into the waste channel 140.

As shown in FIG. 2a, the particle sorting system may also be equipped with a run-dry detector 101. This run-dry detector 101 may use any of the effects mentioned above with respect to FIGS. 1a and 1b, to detect a dry or imminently dry condition within the input channel 120. If the dry or imminently dry condition is detected, the sensor or detector 101 may send a signal to a computer or controller to invoke the stay-wet algorithm. As part of this algorithm, a controlling computer may reverse the flow of fluid within the device. For example, the controller may invert the pressure at point B relative to the pressure at point A, such that the fluid now flows from B to A. Alternatively or in addition, the controller may invert the pressure at point C relative to the pressure at point A, such that the fluid flows from C to A.

There may be other measures taken as a result of the run-dry detector emitting the signal of an imminent dry condition, some of which are discussed in greater detail below. In the case of the laser-induced fluorescence system described here, the stay-wet algorithm may include the disabling or cessation of laser light in laser interrogation region 201. If the laser is not disabled, the heat generated by the laser may heat, evaporate, polymerize or oxidize the components of the sample stream. These components may then become adhered to the walls of the microchannel, thereby altering the flow characteristics or clogging the small channels. This adhered material may also cause cross contamination of samples when a plurality of samples is to be run in the particle sorting system.

Figure 2B:
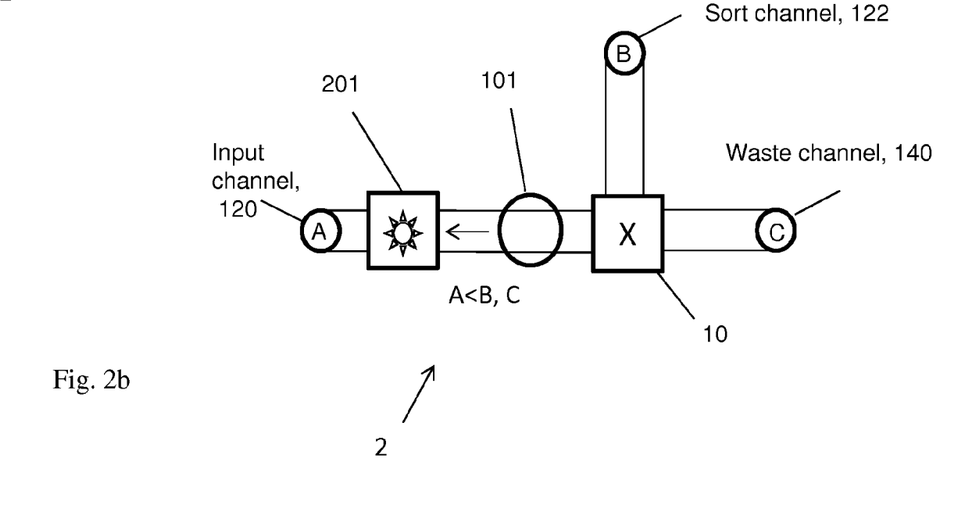
FIG. 2b is a simplified illustration of a stay-wet microfabricated particle sorting system with a run-dry detector in reverse flow.
Figure 3A:
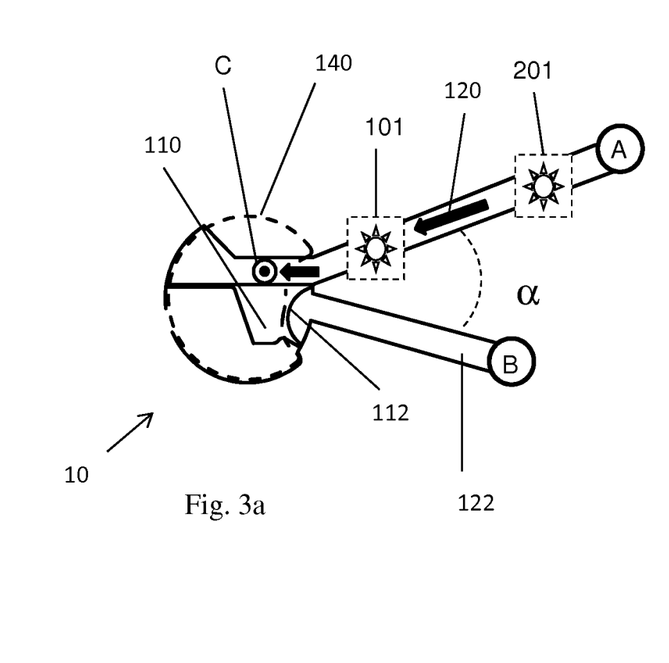
FIG. 3a is a simplified illustration of a stay-wet microfabricated particle sorting system with a run-dry detector and an out-of-plane valve in a first position.
Figure 3B:
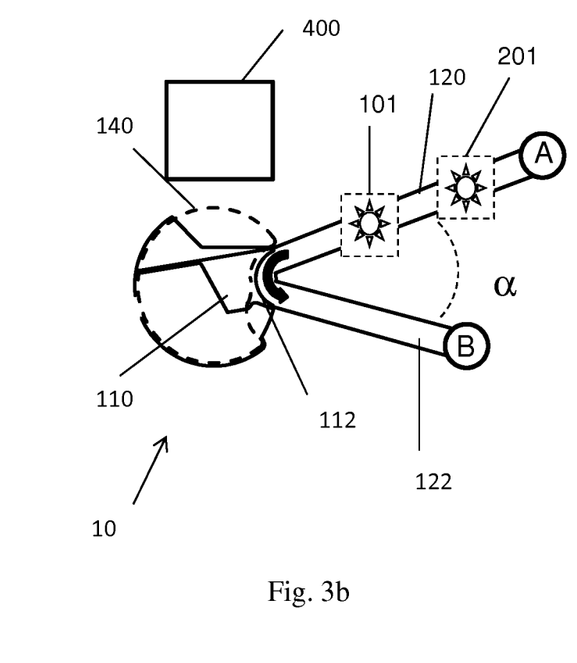
FIG. 3b is a simplified illustration of a stay-wet microfabricated particle sorting system with a run-dry detector and out-of-plane valve in a second (sort) position.

FIG. 3a is a plan view of a particle manipulation system with lithographically formed microfluidic channels and particle sorting stage 10, showing additional details of a novel particle sorting mechanism 10. As such, the system shown in FIGS. 3a and 3b is an embodiment of the system shown generically in FIGS. 2a and 2b. Novel particle manipulation device 10 is described in greater detail in U.S. patent application Ser. No. 13/998,095 (the '095 application), filed Oct. 1, 2013 and assigned to the same assignee as the present application. The '095 application is incorporated by reference in its entirety. As described in detail in the '095 application, the particle sorting device 10 may have at least one output channel, here waste channel 140, which flows in a direction substantially orthogonal to the fabrication plane of the device 10.

The stay-wet particle manipulation systems described here may be particularly suited to this type of out-of-plane type of microfabricated valve. In particular, it has been determined that a microfabricated valve with at least one output channel being disposed out-of-the plane of the sample inlet channel and one other in-plane output channel, may have substantially reduced resistance to fluid flowing backwards through the device, as well as an exceedingly small dead volume. The reduced resistance and small dead volume may minimize the amount of time during which the channel is dry, because the fluid can be very quickly returned to the microchannels. Such an architecture may be particularly advantageous for implementation of the concepts described here.

The device 10 shown in FIG. 3a is in the quiescent (unactuated) position. The device 10 may include a microfabricated fluidic valve or movable member 110 and a number of microfabricated fluidic channels 120, 122 and 140. The fluidic valve 110 and microfabricated fluidic channels 120, and 122 may be formed in a suitable substrate, such as a silicon substrate, using MEMS lithographic fabrication techniques as described in greater detail below and in the '095 application. The fabrication substrate may have a fabrication plane in which the device is formed and the movable member 110 may move in this plane.

A sample stream may be introduced to the microfabricated fluidic valve 110 by a sample inlet channel 120 from sample reservoir A. The sample stream, being formed in the surface of the fabrication substrate, may flow in the plane of that surface. It should be understood that the structures depicted in the accompanying figures may not be drawn to scale, and in fact, the reservoirs may be far larger than the microfluidic channels. The sample stream contained in sample inlet channel 120 may contain a mixture of particles, including at least one desired, target particle and a number of other undesired, nontarget waste particles. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline or bovine serum albumin (BSA). As mentioned, the inlet channel 120 may be formed in the same fabrication plane as the valve 110, such that the flow of the fluid is substantially in that plane. The motion of the valve 110 is also within this fabrication plane.

The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Details as to this detection mechanism are well known in the literature. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

With the valve 110 in the position shown, the inlet stream passes unimpeded to an output orifice and channel 140, which may be out of the plane of the inlet channel 120, and thus out of the fabrication plane of the particle manipulation device 10. Reference C indicates a fluid reservoir and the channel leading therefrom to the movable valve 110. This direction of flow from C is out of the paper as indicated in FIG. 3*a*. That is, the flow is from the inlet channel 120 and sample inlet reservoir A to the output orifice 140, from which it flows substantially vertically into output orifice 140. The flow from C is thus substantially orthogonal to the inlet channel 120, and thus substantially orthogonal to the fabrication plane and the plane of motion of particle manipulation device 10. The flow C into output orifice 140 may therefore be perpendicular to the plane of the paper. More generally, the output channel 140 may not be parallel to the plane of the inlet channel 120 or sort channel 122, or the fabrication plane of the movable member 110.

The output orifice 140 may be a hole formed in the fabrication substrate, or in a covering substrate that is bonded to the fabrication substrate. A relieved area above and below the sorting valve or movable member 110 allows fluid to flow above and below the movable member 110 to output orifice 140. Further, the valve 110 may have a curved diverting surface 112 which can redirect the flow of the inlet stream into a sort output stream. The contour of the orifice 140 may be such that it overlaps some, but not all, of the inlet channel 120 and sort channel 122. By having the contour 140 overlap the inlet channel, and with relieved areas described above, a route exists for the inlet stream to flow directly into the waste orifice 140 when the movable member or valve 110 is in the un-actuated waste position.

Figure 4A:
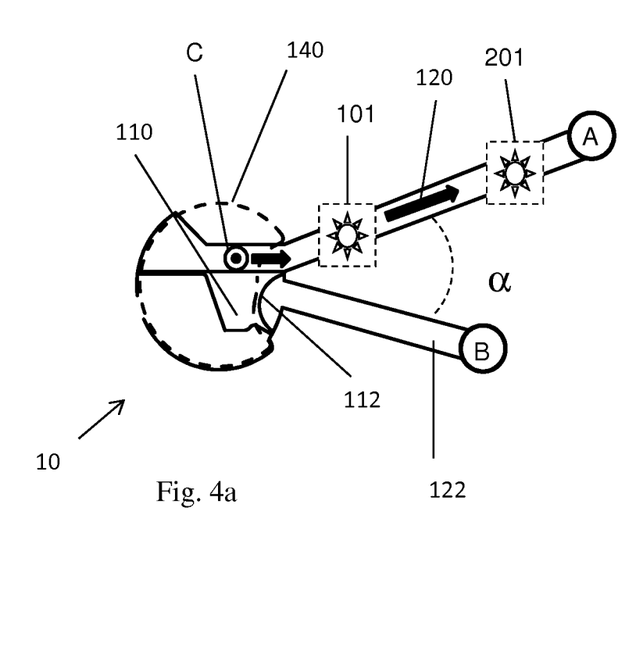
FIG. 4a is a simplified illustration of a stay-wet microfabricated particle sorting system with an out-of-plane valve and a run-dry detector in the input channel, with the flow in the reverse direction between sample inlet channel and waste channel and the fluid valve in the first position.

The device shown in FIG. 3*a* is designed to transport nominally 4 ml of fluid/hour from sample inlet source A to waste orifice C when the valve is in the position shown in FIG. 3*a*, and forward pressure is applied to A relative to C. By reversing the sign of the pressure gradient (i.e. applying higher pressure to C relative to A), the direction of this flow can be reversed, as shown in FIG. 4*a*.

FIG. 3*b* is a plan view of the particle manipulation device 10 in the actuated position. In this position, the movable member or valve 110 is deflected upward into the position shown in FIG. 3*b*.

The output channel 122 may lie in substantially the same plane as the inlet channel 120, such that the flow within the sort channel 122 is also in substantially the same plane as the flow within the inlet channel 120. There may be an angle α between the inlet channel 120 and the sort channel 122. This angle may be any value up to about 90 degrees. In one embodiment, the angle α between the inlet channel 120 and the sort channel 122 may be about 0, meaning that the flows in the two respective channels are essentially antiparallel. The flow in the waste channel 140 may be substantially orthogonal to flow in the sample inlet channel 120 and the sort channel 122. This arrangement may have advantages in terms of minimizing path lengths within the laser interrogation region and reducing resistance to fluid flow as described previously, and so may improve the accuracy of the device.

Figure 4B:
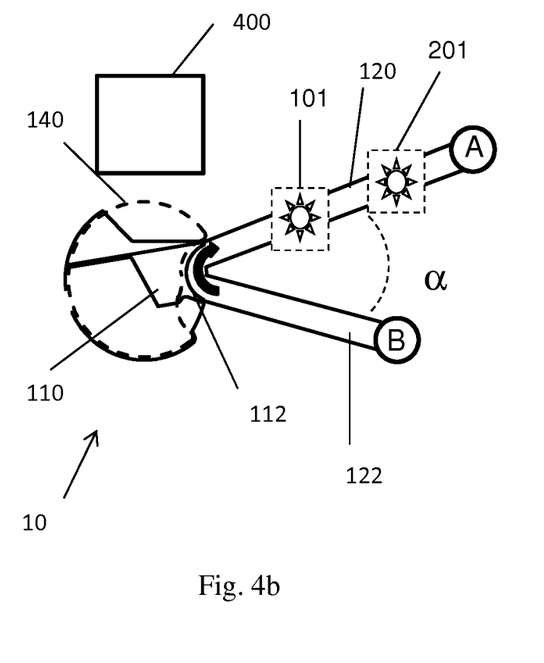
FIG. 4b is a simplified illustration of a constantly wet microfabricated particle sorting system with out-of-plane valve and a run-dry detector in the input channel, with the flow in the reverse direction between sample inlet channel and sort channel and the fluid valve in the second position.

Actuation of movable member 110 may arise from a force from force-generating apparatus 400, shown generically in FIGS. 3*b* and 4*b*. In some embodiments, force-generating apparatus 400 may be a magnet or an electromagnet, however, it should be understood that force-generating apparatus 400 may also be electrostatic, piezoelectric, or some other means to exert a force on movable member 110, causing it to move from a first position (FIG. 3*a*) to a second position (FIG. 3*b*). If magnetic forces are used, the effect may be enhanced by the inclusion of a permeable magnetic feature, such as a region of inlaid NiFe permalloy, inlaid in the movable member. The inlaid feature may be embedded in movable member 110, such that reference number 110 may refer to the movable member as well as the permeable material inlaid therein. The boundary of the inlaid material generally lies just inside of the boundary of the movable member 110. Details as to the design and fabrication of such an inlaid permeable feature may be found in the incorporated '095 application. Magnetic forces arising between this permeable feature and force generating apparatus 400, here an external electromagnet, may produce the motion from the first position (FIG. 3*a*) to the second position (FIG. 3*b*).

More generally, FIGS. 3*a* and 3*b* show a particle manipulation system which includes a particle manipulating device, at least one microfabricated input channel upstream of the particle manipulating device and at least one microfabricated output channel downstream of the particle manipulating device, through which a sample fluid flows, a sensor that detects a dry or imminently dry condition within at least one of the microfabricated channels and puts out a signal when the condition is detected, and a fluid control means for establishing a controlled forward flow between the at least one microfabricated input channel and the at least one microfabricated output channel, and then reversing the flow between the output channel and the input channel upon receiving the signal from the sensor.

The microfabricated particle manipulation system 10 may have a movable member 110 with a diverting surface 112 having a smoothly curved shape, which can redirect the flow of the inlet channel 120 into the sort output channel 122. The diverting surface 112 may be nearly tangent to the input flow direction as well as the sort output flow direction, and the slope may vary smoothly between these tangent lines. With this shape, the moving mass of the stream has a momentum which is smoothly shifted from the input direction to the sort output direction, and thus if the target particles are biological cells, a minimum of force is delivered to the particles. The diverting surface thereby allows flow from the sample inlet channel into the first output (waste) channel when the movable member 110 is in the first position (FIG. 3*a*), and diverts the flow into a second output (sort) channel in the second position (FIG. 3*b*). In other words, a passage between the sample inlet channel and a first output channel (i.e., a waste channel) is formed when the particle sorting mechanism is in a first position (FIG. 3*a*), and a passage between the sample inlet channel and a second output channel (i.e., the sort channel) is formed when the particle sorting mechanism is in the second position (FIG. 3*b*).

It should be understood that although channel 122 is referred to as the "sort channel" and orifice 140 is referred to as the "waste channel" or "waste orifice", these terms can be interchanged such that the sort stream is directed into the waste orifice 140 and the waste stream is directed into channel 122, without any loss of generality. Similarly, the "inlet channel" 120 and "sort channel" 122 may be reversed. The terms used to designate the three channels are arbitrary, but the inlet stream may be diverted by the valve 110 into either of two separate directions, at least one of which does not lie in the same plane as the other two. The term "substantially" when used in reference to an angular direction, i.e. substantially tangent or substantially vertical, should be understood to mean within about 40 degrees of the referenced direction. For example, "substantially orthogonal" to a line should be understood to mean from about 70 degrees to about 110 degrees from the line. The terms "microchannel", "microfabricated channel" and "microfluidic channel" are used interchangeably herein, and refer to a channel containing a fluid flow, and having a characteristic dimension of about 200 microns or less.

In FIG. 3a, a forward pressure was applied between A, B and C, such that flow is from the sample inlet channel A to either sort reservoir B or waste reservoir C. With the movable member 110 in the first position shown in FIG. 3a, the flow is from input A to waste C. With the movable member 110 in the second position shown in FIG. 3b, the flow is from input A to sort B. During normal sorting operation, the flow is as depicted in either FIG. 3a or FIG. 3b.

After a period of normal sorting, the run-dry condition is detected by the run-dry detector 101, which sends the signal to the flow controller to reverse the flow direction. FIG. 4a shows the device in the fluid reversal position, with the pressure reversed between A and C, such that the fluid now flows from C to A. In this situation, the movable member or valve is in the first position, as shown in FIG. 4a. With the valve 110 in the first position, the flow may pass from waste reservoir C back through MEMS particle manipulation mechanism 110, back through interrogation region 201 and back into the sample inlet reservoir A. Accordingly, in one embodiment, the flow may be reversed by the fluid control means with the microfabricated particle sorting mechanism in the first position. The period required for this reverse flow and confirmation may depend on the total volume of fluid contained in the device 10. In one embodiment, the reverse pressure is maintained until substantially all the passageways are filled with fluid. At this point, the pressure valves may be shut, and the fluid may remain stationary within the channels. Any number of measures may then be undertaken, depending on the application. Additional or different sample fluid may be introduced to the device 10, or sort or waste material may be removed, for example.

FIG. 4b shows the device in the fluid reversal position, with the pressure reversed between A and B, such that the fluid now flows from sort reservoir B to sample reservoir A. In this situation, the movable member or valve is in the second position. The volume shown in FIG. 4b can thus be refilled with liquid from the sort channel and sort reservoir B. However, in general, there may be less fluid in the sort reservoir because the target cells are generally rare. Thus, unless the concentration of such cells is known a priori, the total volume of material in the sort reservoir B may not be known. This approach may be more difficult to implement, and may require a calculation based on the fraction of sorted cells, or the total sorted versus the total expected, to determine when the sample reservoir is nearly exhausted. Depending on the number of sorted cells, there may not be a sufficient quantity of fluid to thoroughly re-wet the surfaces of the microfluidic channels using the volume in the sort reservoir, and the waste reservoir would preferably be used to re-wet the surfaces, as was shown in FIG. 4a.

The stay-wet procedure may be particularly suited to the out-of-plane type of microfabricated valve, shown in FIGS. 3a and 3b. In particular, it has been determined that a microfabricated valve with at least one output channel being disposed out-of-the plane of the sample inlet channel and one other in-plane output channel, may have lower resistance to fluid flowing backwards through the device. Because of its low resistance to fluid flow, the reverse flow and interrogation may be performed more quickly, and so with less processing overhead than other valve architectures. Accordingly, such an architecture may be particularly advantageous for implementation of the concepts described here, because even if the channels run-dry, the fluid is reversed very quickly and the fluid volume is returned to the microfluidic channels within a few seconds or less.

Figure 5A:
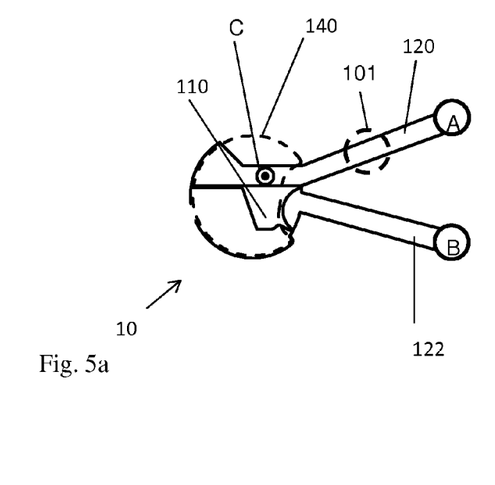
FIG. 5a is a simplified illustration of a stay-wet microfabricated particle sorting system with out-of-plane valve and a run-dry detector in the sample inlet channel.
Figure 5B:
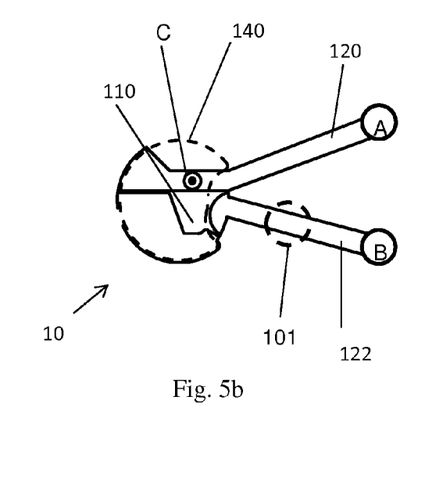
FIG. 5b is a simplified illustration of a stay-wet microfabricated particle sorting system with out-of-plane valve and a run-dry detector in the sort channel.
Figure 5C:
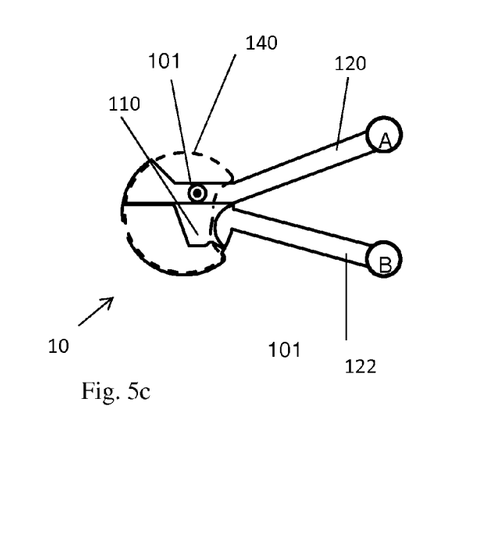
FIG. 5c is a simplified illustration of a stay-wet microfabricated particle sorting system with out-of-plane valve and a run-dry detector in the waste channel.
Figure 5D:
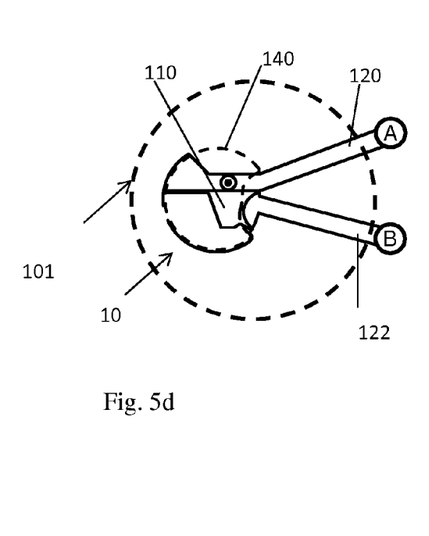
FIG. 5d is a simplified illustration of a stay-wet microfabricated particle sorting system with out-of-plane valve and a run-dry detector having a field of view covering a larger area of the system.

The detector or sensor 101 is shown generically in FIGS. 3a and 3b, and it should be understood that the detector 101 may be based on any number of detection phenomena, some of which are listed here. This list is not meant to be exhaustive, but only to give a number of examples of sensing methodologies. In particular, the detector may detect changes in optical properties, in mechanical properties, electrical or fluid properties. The detector may also monitor the force or energy expended by the pump pumping fluid through the device. Accordingly, the detector or sensor 101 may be placed in any of a number of positions, and some of these alternatives are shown in FIG. 5a-5d. In FIG. 5a, the detector or sensor 101 is disposed in the input channel 120, such that the condition of the input channel 120 is monitored to detect a dry or imminently dry condition. In FIG. 5b, the detector or sensor 101 is disposed in the sort channel 122, such that the condition of the sort channel 122 is monitored to detect a dry or imminently dry condition. In FIG. 5c, the detector or sensor 101 is disposed in the waste channel 140, such that the condition of the waste channel 140 is monitored to detect a dry or imminently dry condition. In FIG. 5d, the detector or sensor 101 is disposed over a larger field of view, covering essentially all three microfluidic channels as well as the movable member 110. It should also be understood that the sensor may be coupled to the fluid control means or the controlling computer, rather than to the microchannels themselves, as described in further detail below.

In one embodiment, the run-dry detector or sensor 101 is a dedicated optical camera which is directed to the interface between the fluid within the channel 120, 122 or 140 and the wall of the channel. It is known that the index of refraction of air is about 1.0, whereas the index of refraction of water is about 1.3. Since the coefficient of reflection from the interface depends on the difference in indices of refraction between two adjacent materials, the amount of light reflected from the interface will change substantially when the fluid within the channel 120, 122 and/or 140 changes to air. The run-dry detector or sensor 101 will put out a signal when a change in the magnitude of light reflected from the interface is detected, indicated that the channel is, or soon will be, dry.

In another embodiment, the run-dry detector 101 may be the optical detector that detects fluorescence from a particle tagged with a fluorochrome. Such fluorescent compounds are routinely conjugated to antibodies in order to identify a particular antigen on a target particle. When a laser is directed on the fluorescent tag, it fluoresces at a longer wavelength, and this fluorescence is detected by a detector, typically a photo multiplier tube (PMT). This same detector, or PMT, may be used to detect a change in the baseline of the light levels, for example, indicating that the channel has, or soon will, run-dry. A suitable detector is described below with respect to FIG. 6.

The device 10 shown in FIGS. 3a, 3b, 4a, 4b, and 5a-5d is designed to transport nominally 4 ml of fluid/hour from sample inlet source A to sort reservoir B when the valve is in the position shown in FIG. 3a, and forward pressure is applied to A relative to B. The total volume of fluid starting in the sample reservoir is generally known. Therefore, in another embodiment, it may also be possible to monitor the weight, fluid level, or condition of the sort, waste or input reservoir, or the duration of the sorting time, or number of events logged, to determine when fluid in the input reservoir is nearly exhausted. More generally, a condition of the input, sort or waste reservoir, or the condition of the channels between these reservoirs and/or the particle manipulation device, may be monitored. By reversing the sign of the pressure gradient (i.e. by lowering the applied pressure to A relative to B and/or C, or by applying higher pressure to B and/or C relative to A) at the point at which the reservoir is nearly empty, the direction of the flow between either the input channel 120 and the sort channel 122 and/or waste channel 140 can be reversed, thus keeping the walls of the microfluidic channels wet at substantially all times. Accordingly, in this embodiment, the sensor may detect the dry or imminently dry condition based on the weight or condition of the input, sort or waste reservoirs, or on a duration of sorting time. Any of these factors may indicate that the sample volume is nearly exhausted.

In yet another embodiment, the run-dry detector may be a sorting controller or computer, that tabulates the sort results and number of events recorded. If the operator knows the approximate number of cells in their sample, the computer may track whether the total number of events has, or shortly will, occur, and send out the signal prompting the system to invoke the stay-wet algorithm. In this embodiment, the run-dry detector 101 may be in the computer which controls the particle manipulation system, as will be described below with respect to FIG. 6. Detection of the run-dry condition is based on the number of events the system has logged, and is therefore a predictor that they microchannels are very likely to soon run dry.

However it is that the run-dry point is determined, the stay-wet algorithm may be invoked when this point is reached. The stay-wet procedure may include a number of steps designed to avoid having the device run-dry for a length of time that the particles in the fluid become adhered to the walls or clog. Or, as described briefly above, it may prevent the microfluidic channels from ever running dry.

It should be understood that by "dry," it is meant that a region within the microchannels includes the local ambient gas in addition to, or instead of the sample liquid. Normally, this ambient gas is air, which infiltrates the system when the sample liquid runs dry. In other cases where other gases are used as input to the system, air might again be the local ambient gas, indicating that the intended fluid or sample gas is being exhausted.

In one embodiment, a fluid control means may be used to control the pressure, and thus the flow, between A, B and C. The fluid control means may be pneumatic or hydraulic, and may include a piston with a pump and associated fluidic passages. The fluid control means may enforce a controlled fluid velocity during normal operation. The controlled velocity may be held constant by the control means, in one embodiment. Or alternatively, the fluid control means may be based on maintaining a constant event rate, such that the fluid velocity changes as a result of changing sample concentrations due to imperfect mixing or cell death for example. The feedback signal may be, for example, the rate of detection or the width of the detected signal. In any case, the fluid control means may be configured to reverse the flow direction from forward to reverse, as described further below.

Figure 6:
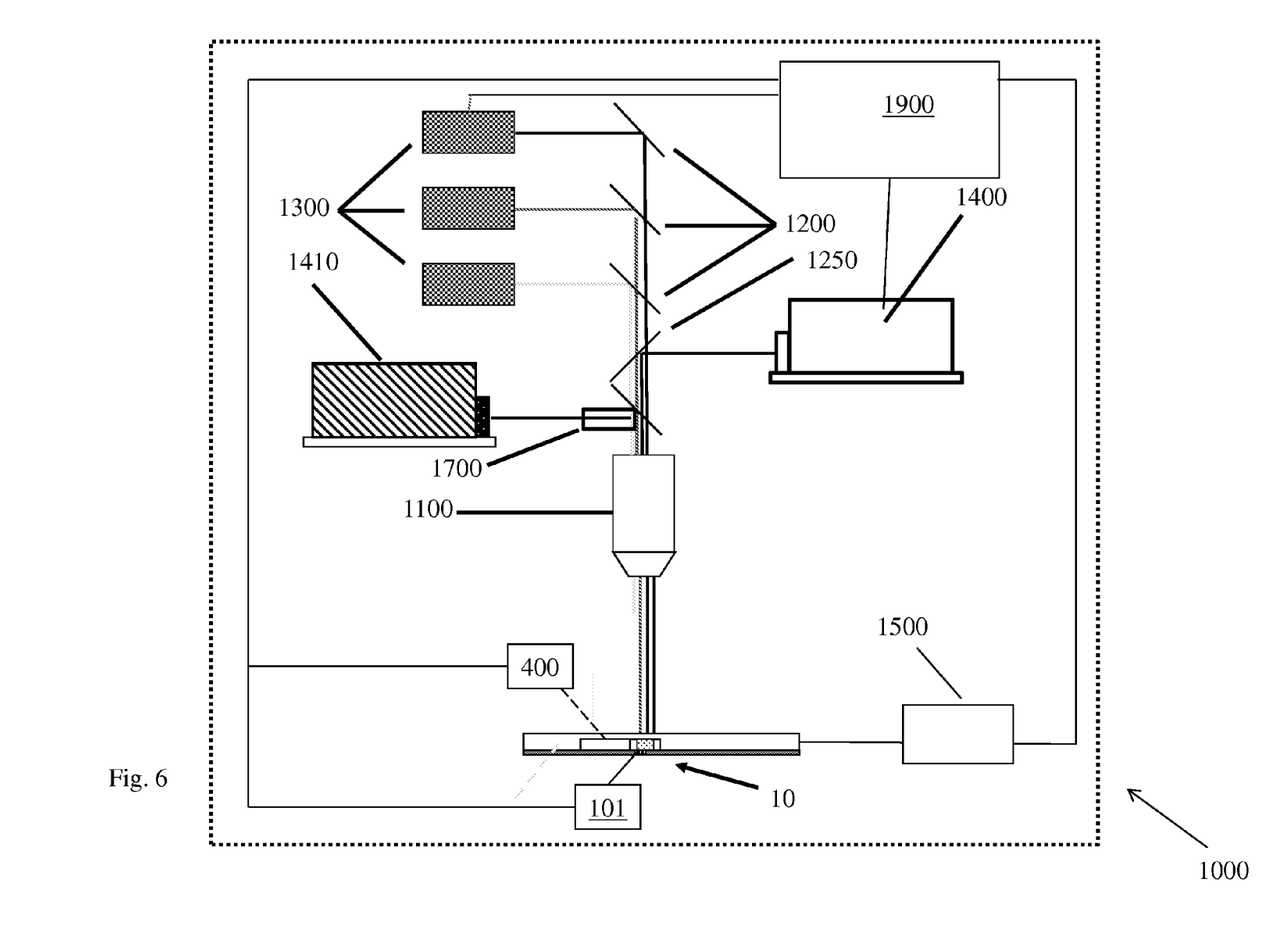
FIG. 6 is a simplified illustration of a microfabricated particle sorting system including the stay-wet detector and control implementation.

FIG. 6 is a schematic illustration of the particle manipulation system 1000 which implements the stay-wet algorithm described above. In particular, FIG. 6 lays out the optical path of the interrogating laser and implementation of the run-dry sensor 101, as well as the control path associated with the stay-wet algorithm. With respect to FIG. 6, normal operation of the system will be described first, then the stay-wet algorithm and implementation will be described as embodied in FIG. 6.

In the normal operation of system 1000, the target particle may be a particular cell, such as a stem cell, or a cancer cell, which has been tagged with a fluorescent marker. This marker emits photons having a particular energy when irradiated with a laser 1400 operating at a predefined wavelength. Accordingly, in this cell sorting system, a laser source 1400 may be directed by a turning mirror 1250 through the detection/collection optics 1100 onto the movable member 110 in the laser interrogation region 201 as was shown in FIG. 3a. The optical axis of the detection/collection optics 1100 and the laser source 1400 may be collinear, at least over a portion of the optical path. Thus, the orientation of the laser application and optical detection along this optical axis may be perpendicular or orthogonal to the substrate fabrication plane, orthogonal to the plane of motion of the movable valve 110 and orthogonal to the flow of the sample fluid through the detection region. This may have important consequences as the light traverses the surfaces with an orthogonal angle of incidence, which may reduce specular reflection and thus reduce or eliminate a noise source in the detection scheme.

The fluorescence emitted from the irradiated particles may be shaped by detection/collection optics 1100 and separated by dichroic mirrors 1200 and directed into a bank of photodetectors 1300. A plurality of photodetectors may accommodate multiple wavelengths of emitted light, for multiparametric detection. The signal output by the photodetectors 1300 indicates the presence or absence of the target particle in the laser interrogation region 201. The signal may be delivered to a controller 1900, which manages the relative timing of the components in the particle sorting system 1000, and collects the data. The controller 1900 may be a general purpose computer or a specialized circuit or ASIC. Upon detection of the target particle, a signal is generated by the controller 1900 which energizes the force-generating or flux-generating apparatus 400. The controller 1900 may also provide the fluidic control to the particle manipulation device 10, via one or more pneumatic, hydraulic, piston-based or mechanical force-based mechanisms.

The force generating apparatus 400 is a device which causes a force to arise in the movable structure 110 itself, causing the motion of the movable structure. This force-generating apparatus 400 may not be directly mechanically coupled to the MEMS particle manipulation device 10, as indicated by the dashed line in FIG. 6. For example, the force-generating apparatus 400 may be a source of magnetic flux which causes a magnetostatic force to arise in an inlaid permeable material in the MEMS particle manipulation device 10. Accordingly, flux generating apparatus 400 may be an electromagnet with a magnetic core and windings. This force may pull the movable valve 110 toward the force-generating apparatus 400, opening the sort channel 122 and closing the waste channel 140, as was shown in FIGS. 3a, 3b, 4a and 4b. Importantly, the force-generating apparatus 400 may reside in the particle sorting system 1000, rather than in the MEMS particle manipulation device 10. As mentioned previously, this may reduce the cost and complexity of the MEMS particle manipulation device 10. Another optional laser 1410 may also be included to provide a second optical channel.

In the laser interrogation region 201, the target particle may be distinguished from the other constituents of the fluid sample. The detection means may be a laser 1400 and associated optics, which directs the laser to a spot upstream of the MEMS movable member 110, and generally in laser interrogation region 201. As mentioned previously, other distinguishing mechanisms may also be used, such as differences in an electrical attribute, a hydrodynamic attribute, a magnetic attribute, an optical attribute, a thermal attribute, mass, and a mechanical attribute of the particle, to name just a few.

Upon passing through the detection region 201, a signal is generated by the detector 1300 indicating that a target particle is present in the interrogation region 201. After a known delay, a signal is generated by the controller 1900 which indicates that the sorting gate, i.e. the movable valve 110 is to be opened, in order to separate the target particle which was detected, from the other components in the fluid stream. The movable MEMS valve 110 may comprise permeable magnetic materials, so that the magnetic force may arise in it in the presence of a magnetic field. When the signal is generated by the controller 1900, a force arises in the embedded magnetically permeable material which draws the movable valve toward the force generating apparatus 400. This motion closes off waste channel 140 and redirects the target particle into a sort channel 122. The sorted sample is subsequently collected from a sort reservoir at the end of the sort channel 122, which holds the sorted sample.

The microfabricated particle manipulation system 10 may be inserted into a housing containing the components shown in FIG. 6. The insertion area may be a movable stage with mechanisms available for fine positioning of the particle manipulation device 10 and associated microfluidic channels against one or more data. These data may orient and position the laser interrogation region 201 and particle manipulation device 10 with respect to the detection/collection optics 1100. If finer positioning is required, the input stage may also be a translation stage, which adjusts the positioning based on observation of the location of the movable diverter 110 or MEMS particle manipulation mechanism 10 relative to the datum.

It should be understood that laser interrogation region 201 may in fact include several laser spots which arise from one or more lasers, and indeed the interrogation need not be a laser at all, but some other distinguishing means based on some other optical, mechanical, or electrical differences for example, as is known in the art of cytometry. As described further below, the distinguishing means may be scattered light or side scattered light which may be based on the morphology of a particle, or may be any number of mechanical, chemical, electric or magnetic effects that can identify a particle as being a target particle. The output of detectors 1300 may be analyzed to separate the content corresponding to different irradiating lasers, or difference fluorescent wavelength excited by the plurality of lasers 1400 and 1410.

A fluid control means 1500 may control the direction and velocity of fluid flowing through the channels of the microfabricated particle manipulation system 10. The fluid control means may be controlled based on a number of criteria as described above. The fluid control means may include pneumatic, hydraulic, and/or one way valves, and/or may include a piston with a pump and associated fluidic passages. During normal operation, the flow may be controlled by the fluid control means 1500 in a feedback loop with controller 1900 to keep fluid velocity, pressure, or event rate constant, for example.

The run-dry detector or sensor 101 may be any of the examples described above, but uses at least one methodology for detecting the condition wherein the microfluidic channel are dry, or imminently dry. Upon detection of this condition, the detector 101 may send a signal to the controller 1900 to invoke the stay-wet algorithm.

Upon receipt of the run-dry signal from detector or sensor 101, the controller 1900 may direct the fluid control means 1500 to reverse the pressure gradient between the sample reservoir and the waste reservoir, for example, as described above. The reverse pressure may persist until it is determined that the microchannels are again filled with fluid. At this point, the controller 1900 may also disable lasers 1400 and 1410, in order to avoid evaporating the remaining fluid, or heating the now stationary fluid. Alternatively, the lasers 1400 and 1410 may be disabled immediately upon receipt of the signal from detector 101, and before the fluid is reversed. Of course, the controller may, in addition, power down any other non-used circuits, total and output sort results, or take any number of additional actions before sorting resumes.

Figure 7A:
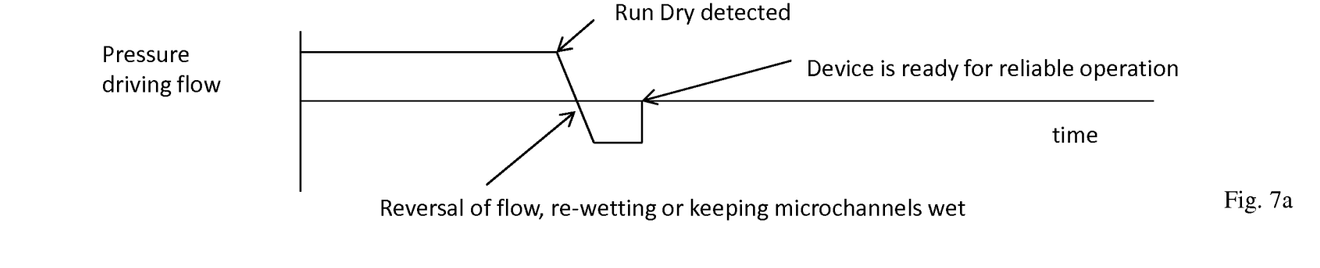
FIGS. 7a, 7b and 7c are exemplary control waveforms which may be applied to the driving pneumatic fluid control means.
Figure 7B:
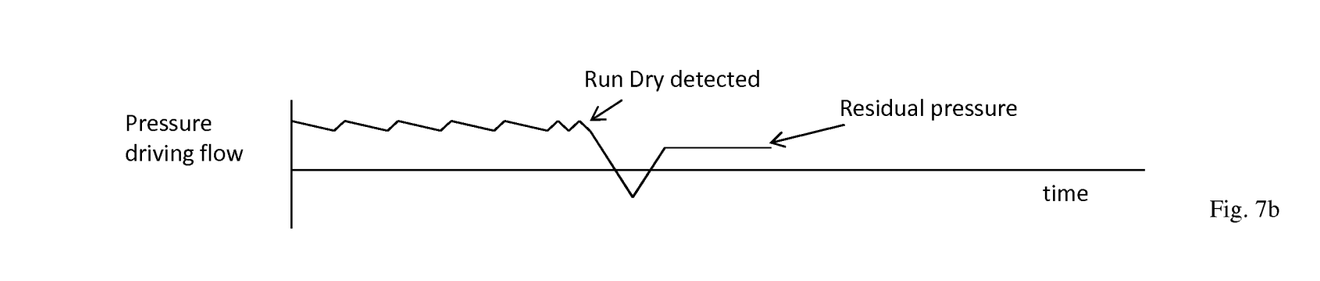
Figure 7C:
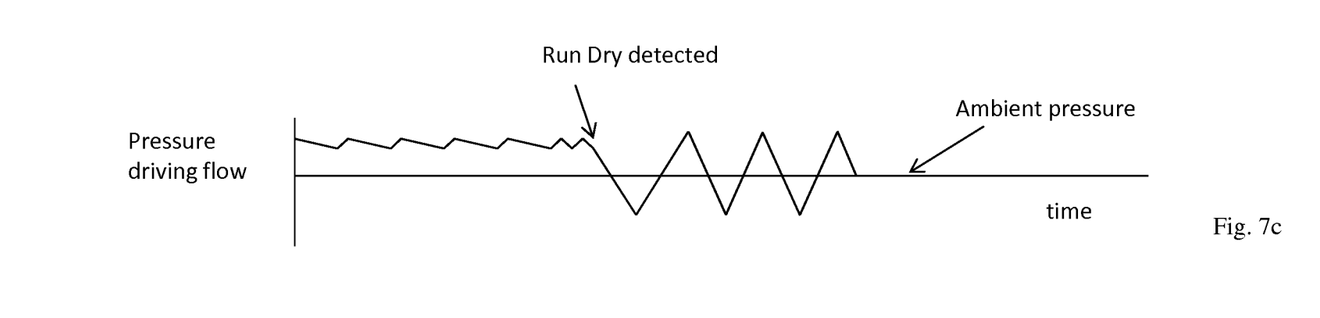

FIGS. 7a, 7b and 7c are diagrams of a control waveform for a stay-wet algorithm as described above. The figure may illustrate the pressure applied between either the sample inlet reservoir and the sort reservoir, or the pressure between the sample inlet reservoir and the waste reservoir. During a first period, sorting continues as usual, until the run-dry detector 101 indicates that the sample reservoir is about to run-dry. When the condition is detected, the run-dry signal is issued, and pressure reverses as shown in FIG. 7a. After a period of running in reverse, the detector determines that the microchannels are again wet, and the driving pressure is terminated. Fluid is allowed to simply remain in the cavities of the device, until sorting is resumed, or some other action is taken.

In FIG. 7b, the condition of the fluid pump is monitored to determine the run-dry condition. The pump may be configured to maintain a constant fluid velocity or a constant event rate, and may be operated in a closed feedback loop in order to keep the fluid velocity tightly controlled. The dry-run condition may be detected by measuring an increase in current consumption, volumetric output, increase in duty cycle, drop in pressure at the output of the pump, or some other condition indicating that the pump and microchannels are running dry. At this point, the pump pressure is reversed and fluid is returned to the cavities in the device. The algorithm may maintain some nominal fluid pressure within the channels relative to atmosphere, so that the fluid is under some pressure, or the pressure may be reduced to ambient, as shown in FIG. 7b.

It should be understood that although the flow rates for the forward fluid direction and the reverse flow direction, and the duration of these flows, is shown as approximately equal in FIGS. 7a and 7b, this is not necessarily the case. In particular, because the cell concentrations may be substantially different and no sorting is taking place during the flow reversal, the reverse fluid velocity may be in excess of the forward velocity. Alternatively, the reverse fluid velocity may be less than the forward rate, in order to reduce the stress on the cells while passing through the microchannels. Finally, instead of leaving the fluid stationary in the channels, the stay-wet algorithm may instead shuttle a quantity of fluid back and forth between the sample reservoir A and the waste reservoir C, or less likely, the sort reservoir B. The constant motion may avoid agglomeration of the particles in the fluid. FIG. 7c shows this embodiment, wherein fluid is shuttled back and forth through the particle manipulation device 10, to keep the components in constant motion until a new sample is added or the operator interferes.

It should be understood that the stay-wet algorithm may apply to all the components of the particle sorting system that have narrow channels. For example, if the sorter is a MEMS-type microfabricated device 10 formed on a substrate, the stay-wet algorithm may be applied to all other fluidic passages coming to or from the MEMS chip that are narrow and thus prone to clogging. These other passages may include plumbing or passages connecting the MEMS chip to the larger fluid reservoirs.

Figure 8:
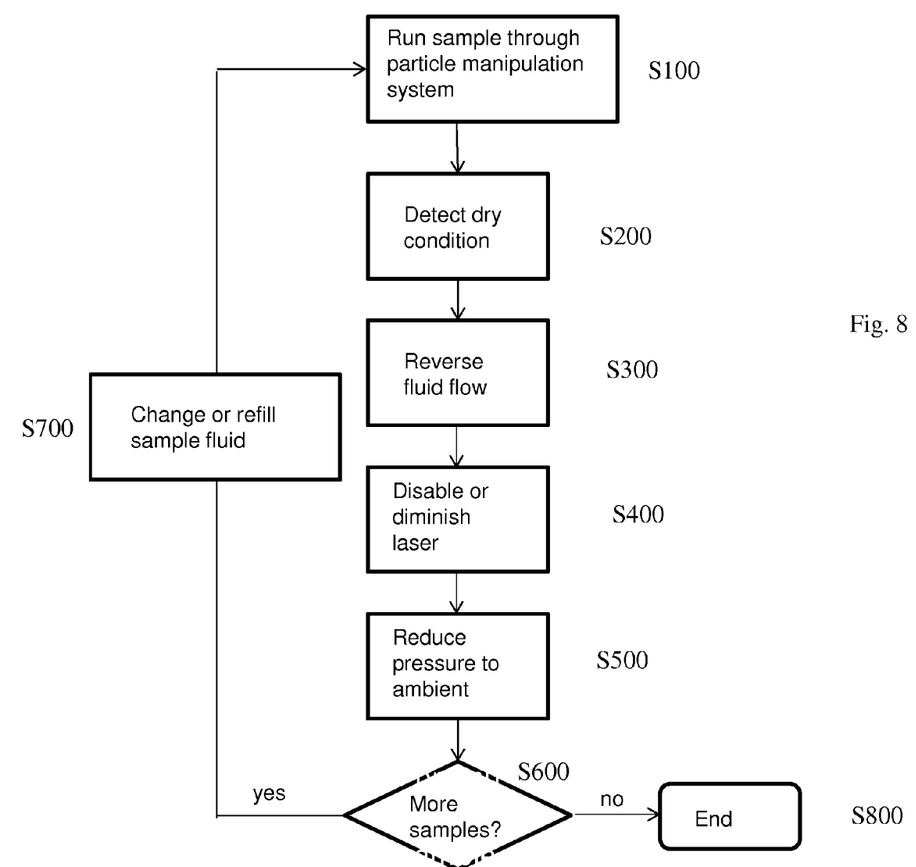
FIG. 8 is an exemplary flow chart of the stay-wet algorithm, which may be used in combination with a microfabricated particle manipulation system according to the present invention.

FIG. 8 shows an exemplary method for performing the stay-wet algorithm. The method begins in step S100, wherein the sample fluid is run through the particle manipulation system. In step S200, a run-dry condition is detected by a sensor, and the sensor sends a signal to this effect. In step S300, the flow is reversed in the system. In step S400, the laser is diminished or disabled. As mentioned previously, it should be understood that step S400 may precede step S300, such that the laser is disabled or diminished immediately upon receiving the signal in step S200, and before the flow is reversed. In step S500, the driving pressure is reduce to ambient, for example, such that the fluid ceases to flow. In step S600, a determination is made whether additional samples are waiting to be run. If yes, the samples are changed in step S700 and the process returns to the beginning, S100. If no, the method ends in step S800.

It should be understood that all of the steps shown in FIG. 8 may not be necessary, for example, step S400 the laser disabling may be omitted if no laser is being used or if the run-dry condition is expected to have a limited duration. Similarly, the steps need not be performed in the order indicated, for example, the laser may be disabled before the flow is reversed. Instead of, or in addition to step S400, the method may also include reducing an output of an interrogation laser, disabling, reducing, reversing a pump output, sounding an audible alarm, and sending a warning message to a computer monitor.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A particle manipulation system, comprising:
   a particle manipulating device fabricated on a silicon substrate;
   at least one microfabricated input channel upstream of the particle manipulating device and a sort output channel and a waste output channel downstream of the particle manipulating device, through which a sample fluid flows;
   a sensor that detects a dry or imminently dry condition within at least one of the microfabricated channels and puts out a signal when the condition is detected;
   a fluid control device for establishing a controlled forward flow between the at least one microfabricated input channel and at least one of the sort output channel and waste output channel, and then reversing the flow upon receiving the signal from the sensor; and
   wherein the particle manipulating device moves from a first position to a second position in response to a force, and wherein the motion is substantially in a plane parallel to the surface of the substrate and wherein at least one of the sort channel and the waste channel is substantially orthogonal to the surface and directly below at least a portion of the particle manipulating device over at least a portion of its motion.

2. The particle manipulation system of claim 1, wherein the particle manipulating device comprises a microfabricated particle sorting mechanism formed on a surface of a substrate, and the sample fluid comprises target particles and non-target material.

3. The particle manipulation system of claim 2, wherein the microfabricated particle sorting mechanism moves to divert target particles from the microfabricated input channel into a microfabricated sort output channel in response to a force, and wherein the motion of the particle sorting mechanism to divert the target particles is substantially in a plane parallel to the surface of the substrate.

4. The particle manipulation system of claim 3, wherein flow in the input channel is substantially antiparallel to flow in the microfabricated sort output channel, and the force is a magnetic force, and wherein a waste output channel is substantially orthogonal to the input channel and the sort output channel, and wherein flow is reversed by the fluid control means between the waste channel and the input channel when the signal is received from the sensor.

5. The particle manipulation system of claim 2, wherein the microfabricated particle sorting mechanism further comprises:
   a permeable magnetic material inlaid in the microfabricated particle sorting mechanism; and
   a source of magnetic flux external to the microfabricated particle sorting mechanism and substrate on which the microfabricated particle sorting mechanism is formed, wherein the magnetic flux interacts with the inlaid permeable magnetic material to move the microfabricated particle sorting mechanism, whereby the microfabricated particle sorting mechanism moves from a first position to a second position when the source of magnetic flux is activated.

6. The particle manipulation system of claim 1, wherein the sensor detects the dry or imminently dry condition based on at least one of fluid pressure, optical properties, viscosity, capacitance, and fluid resistance within at least one of the microfabricated channels.

7. The particle manipulation system of claim 1, wherein the sensor detects the dry or imminently dry condition based on at least one of a condition of an input, sort or waste reservoir, or condition of the channels between these reservoirs and the particle manipulation device, or a duration of sorting time or a number of events the system has logged.

8. The particle manipulation system of claim 3, wherein when the microfabricated particle sorting mechanism is in the first position, a passage between the microfabricated input channel and a waste channel is formed, and when the microfabricated particle sorting mechanism is in the second position, a passage between the microfabricated input channel and the microfabricated sort output channel is formed.

9. The particle manipulation system of claim 8, wherein the fluid control device reverses the direction of fluid flow with the microfabricated particle sorting mechanism in the first position.

10. The particle manipulation system of claim 8, wherein the fluid control device reverses the direction of fluid flow with the microfabricated particle sorting mechanism in the second position.

11. The particle manipulation system of claim 2, further comprising: a controller which controls the fluid control device to maintain a forward flow direction during normal sorting, and reverses the fluid direction upon receiving the signal from the sensor.

12. The particle manipulation system of claim 11,
   wherein the controller invokes a stay-wet algorithm upon receiving the signal from the sensor; and
   wherein the stay-wet algorithm includes at least one of: reducing, altering or disabling an output of an interrogation laser; reducing, altering or disabling a power supply output; reducing, disabling or reversing a pump output; sounding an audible alarm; and sending a warning message.

13. A method for manipulating particles with a particle manipulation device, comprising:
   providing a particle manipulating device on a surface of a substrate;
   providing at least one microfabricated input channel upstream of the particle manipulating device and a sort output channel and a waste output channel downstream of the particle manipulating device, flowing a fluid through microfabricated input channel to the at least one microfabricated sort or waste output channel during normal operation;

sensing that a microfluidic channel is about to or is running dry;

outputting a signal indicative of a run-dry condition;

reversing the flow between the at least one microfabricated input channel and the at least one sort output channel and waste output channel, upon receiving the signal; and wherein the particle manipulating device moves from a first position to a second position in response to a force, and wherein the motion is substantially in a plane parallel to the surface of the substrate and wherein at least one of the sort channel and the waste channel is substantially orthogonal to the surface and directly below at least a portion of the particle manipulating device over at least a portion of its motion.

14. The method of claim 13, wherein the particle manipulating device comprises a microfabricated particle sorting mechanism formed on a surface of a substrate, and the sample fluid comprises target particles and non-target material.

15. The method of claim 13, wherein the microfabricated particle sorting mechanism moves to divert target particles from a microfabricated input channel into a microfabricated sort output channel in response to a force, and wherein the motion of the particle sorting mechanism to divert the target particles is substantially in a plane parallel to the surface of the substrate, and wherein the microfabricated particle sorting mechanism moves from a first position to a second position to divert the particles when the force is applied.

16. The method of claim 13,
wherein in response to the signal indicative of the run-dry condition, the method further comprises the steps of:
reducing, altering or disabling an output of an interrogation laser, reducing, altering or disabling a power supply output; reducing, disabling or reversing a pump output; sounding an audible alarm; and sending a warning message.

17. The method of claim 13, wherein the sensing that a microfluidic channel is about to run-dry comprises detecting a change in at least one of fluid pressure, optical properties, viscosity, capacitance, fluid resistance within at least one of the microfabricated channels, and that the sample volume is nearly exhausted.

18. A method for manipulating particles with a particle manipulation device, comprising:
providing a particle manipulating device;
providing at least one microfabricated input channel upstream of the particle manipulating device and at least one microfabricated output channel downstream of the particle manipulating device,
flowing a fluid through microfabricated input channel to the at least one microfabricated output channel during normal operation;
sensing that a microfluidic channel is about to or is running dry;
outputting a signal indicative of a run-dry condition; and
reversing the flow between the at least one microfabricated input channel and at least one microfabricated output channel, upon receiving the signal,
wherein the particle manipulating device comprises a microfabricated particle sorting mechanism formed on a surface of a substrate, and the sample fluid comprises target particles and non-target material,
wherein the microfabricated particle sorting mechanism moves to divert target particles from a microfabricated input channel into a microfabricated sort output channel in response to a force, and wherein the motion of the particle sorting mechanism to divert the target particles is substantially in a plane parallel to the surface of the substrate, and
wherein the microfabricated particle sorting mechanism moves from a first position to a second position to divert the particles when the force is applied,
wherein flow in the input channel is substantially antiparallel to flow in the sort output channel, and wherein the force is a magnetic force,
and wherein a waste output channel is substantially orthogonal to the input channel and the sort output channel, and
wherein flow is reversed between the waste channel and the input channel when the signal is received from the sensor.

19. The method of claim 18, reversing the flow comprises reversing the direction of fluid flow with the microfabricated particle sorting mechanism in the first position.

* * * * *